United States Patent [19]
Kawahara et al.

[11] Patent Number: 5,395,321
[45] Date of Patent: Mar. 7, 1995

[54] INFUSION APPARATUS CAPABLE OF STORING A PLURALITY OF ACCUMULATED INFUSION FLUID VOLUMES OF THE PAST

[75] Inventors: Masafumi Kawahara, Nara, Japan; Thomas Callaghan; Grace M. Esche, both of Algonquin, Ill.; Cynthia A. Bennett, Park Ridge, Ill.

[73] Assignees: Sharp Kabushiki Kaisha, Osaka, Japan; Baxter International Inc., Deerfield, Ill.

[21] Appl. No.: 42,005

[22] Filed: Apr. 2, 1993

[30] Foreign Application Priority Data

Apr. 3, 1992 [JP] Japan .................................. 4-081976

[51] Int. Cl.⁶ ...................... A61M 31/00; A61M 1/00
[52] U.S. Cl. ...................... 604/67; 604/153; 128/DIG. 13
[58] Field of Search ...................... 604/65–67, 604/151–155, 189; 128/DIG. 12, DIG. 13

[56] References Cited

U.S. PATENT DOCUMENTS

| | | | |
|---|---|---|---|
| 4,074,356 | 2/1978 | Schiller et al. | 364/465 |
| 4,328,549 | 5/1982 | Avery | 364/469 |
| 4,432,020 | 2/1984 | Onose et al. | |
| 4,469,481 | 9/1984 | Kobayashi | 604/67 |
| 4,670,007 | 6/1987 | Wheeldon et al. | 604/65 |
| 4,715,786 | 12/1987 | Wolff et al. | 417/22 |
| 4,928,701 | 5/1990 | Harada et al. | 128/677 |
| 5,051,920 | 9/1991 | Reams et al. | 364/509 |
| 5,089,961 | 2/1992 | Coble et al. | 364/413.02 |
| 5,277,196 | 1/1994 | Hankinson et al. | 128/725 |
| 5,279,303 | 1/1994 | Kawamura et al. | 128/683 |

Primary Examiner—John D. Yasko
Assistant Examiner—Adam J. Cermak

[57] ABSTRACT

In an infusion apparatus for use in the medical field, a peristaltic pump mechanism pumps an infusion fluid including medication through an administration tube toward a patient. A clock powered independent of the apparatus counts a predetermined unit time. A CPU accumulates data representing an incremental unit of fluid of the infusion fluid delivered by the pump mechanism to measure an accumulated infusion fluid volume each time the clock counts the unit time. Data as to the current accumulated infusion fluid volume is stored in a second storage section of a RAM. Each time the clock counts the unit time, data representing the accumulated infusion fluid volume stored in the second storage section is written to a ring buffer in the RAM, so that the ring buffer stores data representing a plurality of accumulated infusion fluid volumes in one-to-one correspondence with a plurality of times at which the plurality of accumulated infusion fluid volumes were measured. The CPU accesses the buffer ring at a key-inputted request by an operator to display any desired accumulated data of the infusion fluid volume on a display unit.

5 Claims, 8 Drawing Sheets

Fig. 2

Vistpnt : Vi store pointer
Violdpnt: Vi oldest data pointer
Virdpnt : Vi readout pointer

Fig. 5 n: 10 hours and 1 minute ago
m: 10 hours ago

Virdpnt

INFUSION APPARATUS CAPABLE OF STORING A PLURALITY OF ACCUMULATED INFUSION FLUID VOLUMES OF THE PAST

BACKGROUND OF THE INVENTION

1. Field of the Invention

The present invention relates to an infusion apparatus for use in the medical field and more particularly to an infusion apparatus capable of storing an accumulated volume of infusion fluid already delivered as well as settings such as infusion rate and volume of infusion fluid to be delivered.

2. Description of the Prior Art

Figure 6:
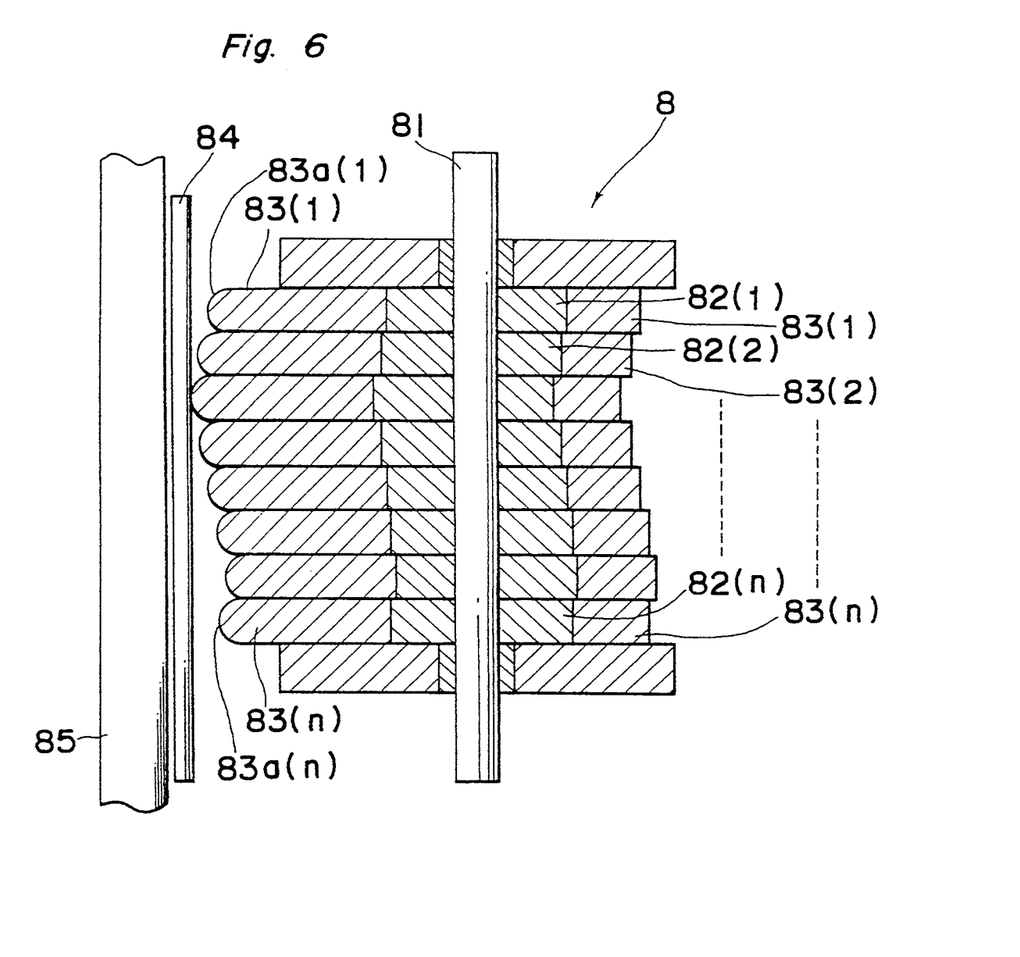
FIG. 6 is a cross-sectional view of a pump mechanism commonly used in infusion apparatuses and also used in the embodiment of FIG. 1.

Infusion apparatuses are used for administering medication such as saline solution into a vein of a patient. A generally known infusion apparatus is of an electromechanical positive pressure peristaltic type provided with a pump mechanism for peristaltically delivering medication. FIG. 6 shows an example of such a pump mechanism. The pump mechanism, generally indicated by numeral 8 in FIG. 6, has n pressure fingers 83(1), 83(2), . . . , 83(n) with their ends 83a(1), . . . , 83a(n) confronting a door 85 of a housing of the infusion apparatus, and n cams 82(1), 82(2), . . . , 82(n) associated with the n pressure fingers 83(1), 83(2), . . . , 83(n). The cams 82(1), 82(2), . . . , 82(n) are engaged with a shaft driven by a not-shown stepping motor, with their phases shifted from one another. The pressure fingers 83(1), 83(2), . . . , 83(n) are individually moved in sequence toward the door 85 by the associated cams 82(1), 82(2), . . . , 82(n) with rotation of the shaft 81 so as to push an administration tube 84 set in the pump mechanism against the door 85. By so pressing the administration tube 84 against the door 85 from above downward with the fingers 83(1), 83(2), . . . , 83(n), medication supplied from an administration set into the administration tube 84 is peristaltically delivered to a patient.

Figure 7:
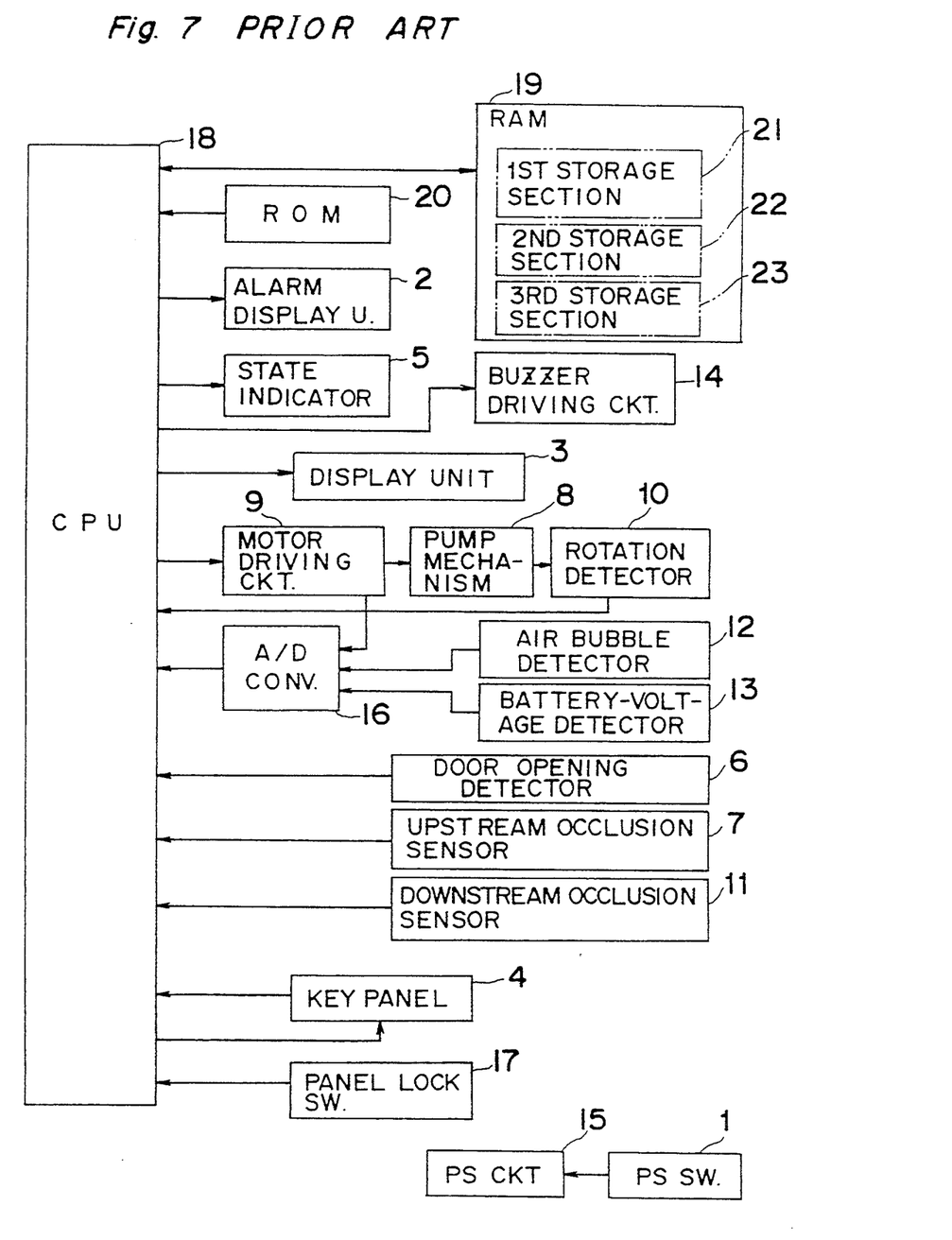
FIG. 7 is a block diagram of a conventional infusion apparatus.
Figure 8:
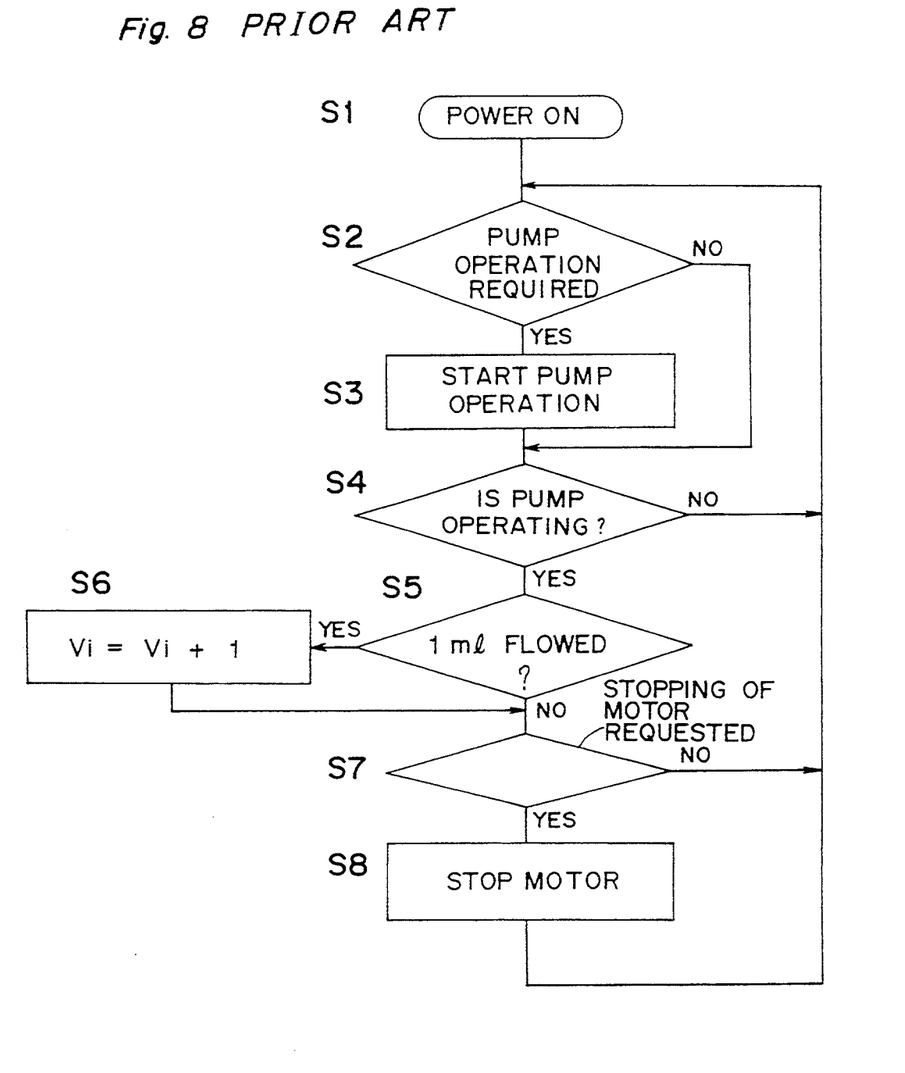
FIG. 8 is a flowchart of the operation of the conventional infusion apparatus of FIG. 7.
Figure 9:
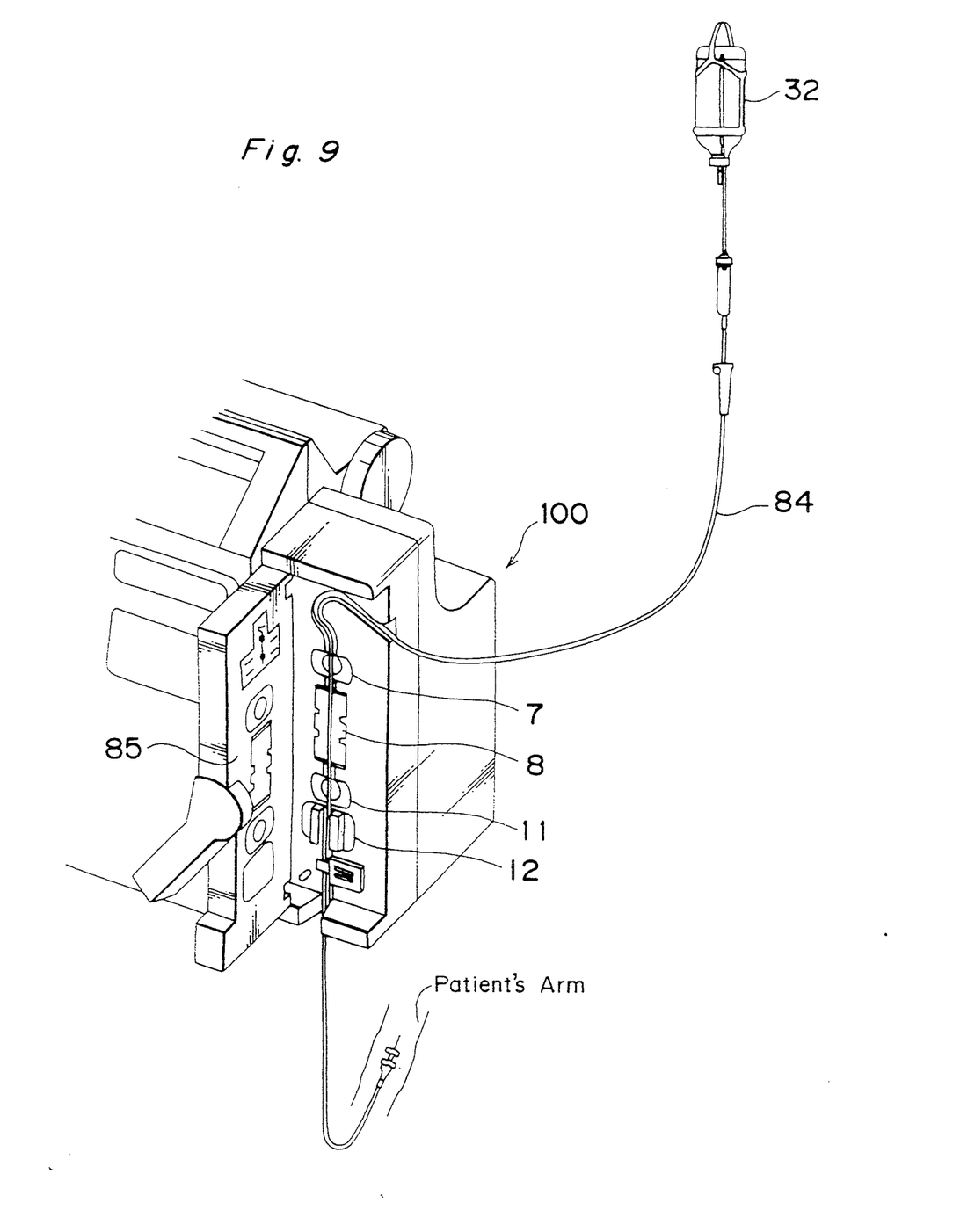
FIG. 9 is a perspective view showing a common infusion apparatus.

FIG. 7 shows a block diagram of a conventional infusion apparatus of the above-mentioned type, FIG. 8 is a flowchart showing the operation of the infusion apparatus of FIG. 7, and FIG. 9 is a perspective view showing a part of the infusion apparatus. It is to be noted that because an infusion apparatus of the present invention described later has a similar appearance, FIG. 9 is also used to illustrate the infusion apparatus of the present invention.

Referring to FIG. 7 and FIG. 9, a power switch 1 turns on the infusion apparatus, generally indicated by numeral 100, when pressed. An alarm display unit, designated by numeral 2, displays all alarm messages for errors detected in the infusion apparatus. A display unit, designated by numeral 3, displays infusion-related parameters such as a volume of infusion fluid delivered per unit time (simply referred to as "infusion rate" or "delivery rate" below), total volume of infusion fluid to be delivered at the infusion rate (simply referred to as "volume to be delivered" or "volume to be infused" hereinafter), as well as an accumulated value of the infusion fluid delivered (referred to simply as "accumulated infusion fluid volume" hereinafter). A key panel, designated by numeral 4, has thereon numeral keys for inputting settings such as the infusion rate and volume to be delivered to set values of operation speed and operation time for the pump mechanism 8, control keys for input assistance, a start key for starting the operation of the pump mechanism 8, a stop key for stopping the operation of the pump mechanism 8, and a call key for requesting various values such as the accumulated infusion fluid volume to be displayed. A state indicator, designated by numeral 5, is a lamp that indicates which state the apparatus is currently in among the states of "alarming", "in operation", and "out-of-operation". A door opening detector, designated by numeral 6, detects whether or not the door 85 has come into an open position in which the administration tube 84 is set in place in the pump mechanism 8. The door opening detector 6 also detects that the door 85 is inadvertently opened while the pump mechanism 8 is in operation. When this error is detected, the operation of the pump mechanism 8 is stopped and an alarm is raised. An upstream occlusion sensor, designated by numeral 7, detects a pressure-reduction state caused by occurrence of any abnormality (e.g., clogged filter) in the administration set disposed between a medical fluid container 32 and the apparatus. A motor driving circuit, designated by numeral 9, drives the stepping motor of the pump mechanism 8 in response to a pulse outputted from a CPU 18. A rotation detector, designated by numeral 10, through detection of the amount of rotation of the stepping motor of the pump mechanism 8 detects that an incremental unit (e.g., 1 ml) of fluid has taken place, and then informs the CPU 18 of it. A downstream occlusion sensor, designated by numeral 11, detects a pressure-rise state within the administration tube 84 located between the apparatus and the patient to detect occurrence of any abnormality such as occlusion occurring within the administration tube 84. When the pressure-rise state is detected, the pump mechanism 8 is stopped and an alarm is raised. An air bubble detector, designated by numeral 12, detects that air bubbles of more than a prescribed amount have entered the administration tube 84. When this is detected, an alarm is raised while the pump mechanism 8 is stopped so that the bubbles are prevented from entering into the patient's body. A battery-voltage detector, designated by numeral 13, detects any battery-voltage drop of a lead battery (not shown) used as a backup of an AC power supply. When this battery-voltage drop is detected, operation of the pump mechanism 8 is stopped while an alarm is raised. The lead battery is charged by a power supply circuit 15 when the apparatus is fed power from the AC power supply. A buzzer driving circuit, designated by numeral 14, generates a buzzer sound for informing doctors and nurses of the fact that the infusion apparatus has entered into the alarming state. The power supply circuit 15 supplies power to all the circuits of the infusion apparatus. An analog-to-digital converter, designated by 16, converts analog data such as the voltage resulting from voltage conversion of a current supplied to the motor of the pump mechanism 8, the air bubble detector output level, and the battery voltage level into digital values, and inputs them into the CPU 18. A panel lock switch, designated by numeral 17, serves to render the panel keys and the power key input-inhibited so that the infusion apparatus will not be operated by unauthorized personnel. The CPU 18 controls the operation of the overall infusion apparatus. A RAM (memory section), designated by numeral 19, includes a first storage section 21 for storing infusion-related parameters such as infusion rate and volume to be infused, those parameters having been key-inputted, a second storage section 22 for storing a current accumulated value Vi of unit flows of the infusion fluid, i.e., accumulated infusion fluid volume, detected by the rotation detector 10, and a third storage section 23 for storing various types of data used for arithmetic operations by the CPU 18. A ROM (program section), designated by numeral 20, contains a program for operating the CPU 18.

The following describes the operation of the conventional infusion apparatus with reference to the flowchart shown in FIG. 8.

When the infusion apparatus 100 is turned on at step S1, it is determined at step S2 whether or not the pump operation has been requested. When the apparatus becomes ready, the program proceeds to step S3 to start operation of the pump mechanism 8. Then the program proceeds to step S4 at which it is determined whether or not the pump mechanism 8 is in operation. When the pump mechanism 8 is in operation, the program proceeds to step S5. When it is detected by the rotation detector 10 that there was an incremental unit of fluid (1 ml in this case), the accumulated infusion fluid volume Vi is incremented by one (Vi=Vi+1) at step S6. The value of the accumulated infusion fluid volume Vi is renewed until it is detected at step S7 that there was a request for stopping the motor of the pump mechanism. When the motor is requested to stop, the motor is stopped at step S8.

When medication is administered to a patient using the infusion apparatus, parameter values of the infusion rate and volume to be infused are set first, and according to those parameter values the administration operation repetitively starts and stops.

However, in the aforementioned conventional infusion apparatus, which stores only the latest value of the renewed accumulated infusion fluid volume as a value indicating a history of the infusion treatment or fluid therapy, it is impossible to correctly perceive how long the infusion operation was effected in the past, whether the infusion fluid was delivered at an even rate throughout the operation time, or whether the infusion fluid was delivered at different rates based on a plurality of settings of the infusion rate and volume to be delivered. Therefore, while operating the infusion apparatus, an operator (doctor or nurse) had to manually record data such as actual infusion rate and volume of delivered infusion fluid to record a history of the infusion. This was time consuming for the operator and increased the opportunity for recording errors which could result in an adverse effect on the medical treatment to the patient.

SUMMARY OF THE INVENTION

The object of the present invention is therefore to provide an infusion apparatus obviating the need for manually recording the process of the infusion by storing a plurality of accumulated infusion fluid volumes measured at different times of the past.

In order to achieve the aforementioned object, an embodiment of the present invention provides an infusion apparatus for infusing an infusion fluid into a patient through an administration tube, comprising (a) a pump mechanism for peristaltically pumping the infusion fluid in the administration tube to deliver the infusion fluid toward the patient, (b) clock means for counting a predetermined unit time, (c) accumulating means for accumulating a unit flow, i.e., an incremental unit of fluid, of said infusion fluid delivered by said pump mechanism to measure an accumulated infusion fluid volume each time said clock means counts said predetermined unit time, (d) storage means for storing a plurality of accumulated infusion fluid volumes measured by said accumulating means, each accumulated infusion fluid volume being written in sequence into said storage means each time said clock means counts said predetermined unit time, (e) accessing means for reading out any one of said accumulated infusion fluid volumes stored in said storage means at a request of an operator, (f) display means for displaying the accumulated infusion fluid volume read out by said accessing means, (g) means for inputting said request.

In an embodiment, the above storage means is constructed of a ring buffer which always holds a predetermined number of newest accumulated infusion fluid volumes measured in a predetermined period of time preceding a current time. The plurality of accumulated infusion fluid volumes stored in the ring buffer is in one-to-one correspondence with a plurality of different times at which those accumulated infusion fluid volumes were measured.

With this infusion apparatus of the invention, the operator, more specifically a doctor or nurse, can readily call and display the accumulated infusion fluid volumes stored in the storage means on the display means in chronological order or in arbitrary order. From the displayed data, the operator can obtain infusion-related information such as infusion rates adopted in the past, volume of the infusion fluid delivered during a specific period of time in the past, etc. That is, the operator can know a history of the infusion treatment applied to the patient. Therefore, the operator does not need to manually record the infusion rate and volume of the delivered infusion fluid.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE PREFERRED EMBODIMENTS

The following describes the present invention with reference to an embodiment shown in the attached drawings.

Figure 1:
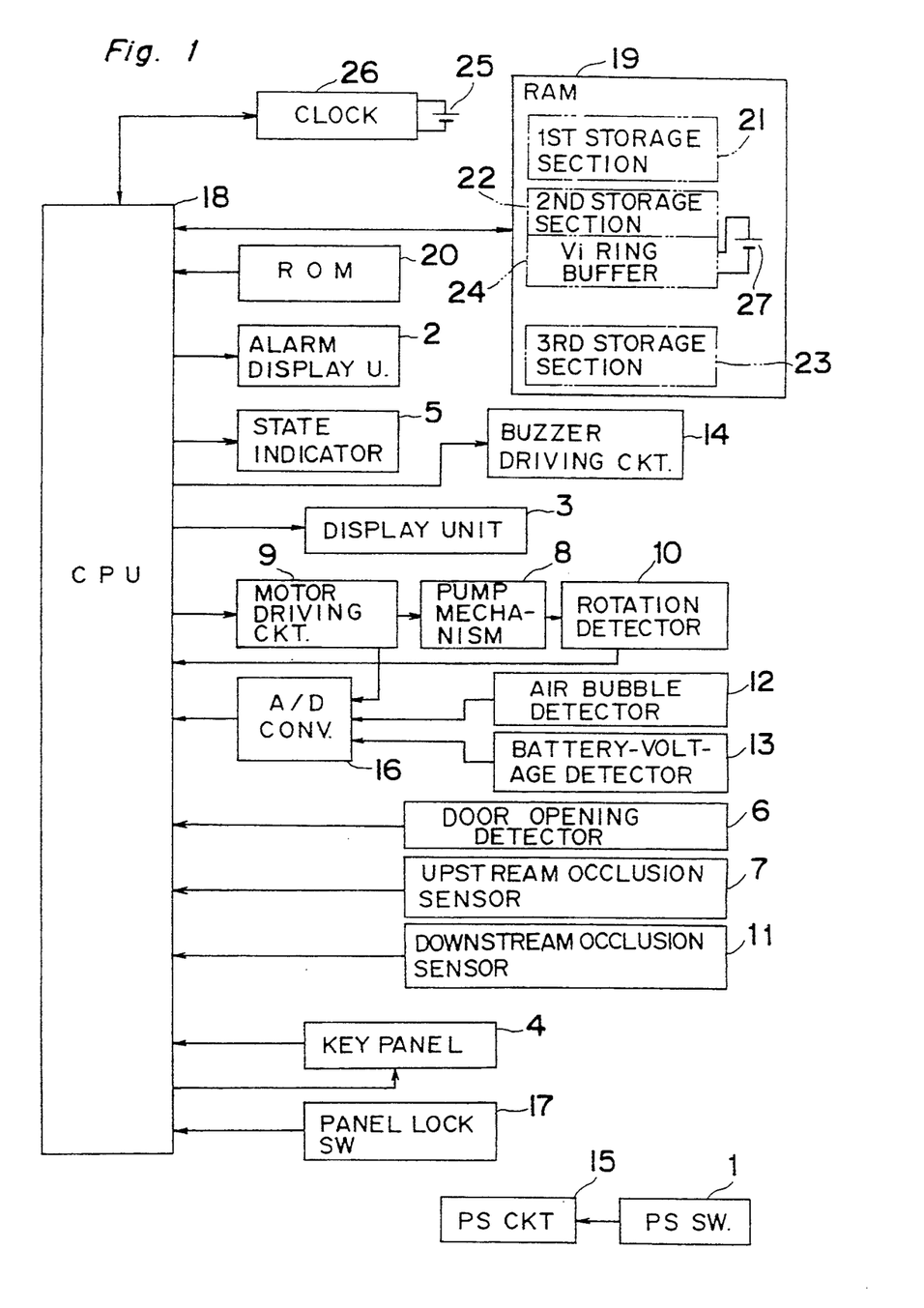
FIG. 1 is a block diagram of an infusion apparatus according to an embodiment of the present invention.

FIG. 1 is a block diagram of an infusion apparatus according to an embodiment of the present invention. In FIG. 1, parts similar to the parts of FIG. 6 are indicated by the same reference numeral used in FIG. 6 and a detailed description on those parts is omitted here.

In addition to the constituents of the conventional infusion apparatus of FIG. 6, the infusion apparatus of the present embodiment incorporates a clock 26 which operates on a lithium battery 25 independent of a power supply for the infusion apparatus. Furthermore, a RAM (memory section) 19 incorporated in this embodiment further has a Vi buffer ring (simply referred to as "ring buffer" hereinafter) 24 capable of storing 1500 ($60 \times 25 = 1500$) values so that accumulated infusion fluid volumes Vi are written to the buffer ring 24 one by one each time one minute (unit time) elapses during a period of 25 hours. Therefore, the RAM 19 can store not only the latest accumulated infusion fluid volume value in the second storage section 22 as done in the conventional infusion apparatus but also sequential accumulated infusion fluid volumes written in the last 25 hours in the ring buffer 24. The Vi buffer ring 24 is backed up by power from a lithium battery 27. The CPU 18 reads out a value stored in the ring buffer 24 at a request inputted by the call key on the key panel 4 to display the value on the display unit 3.

Figure 2:
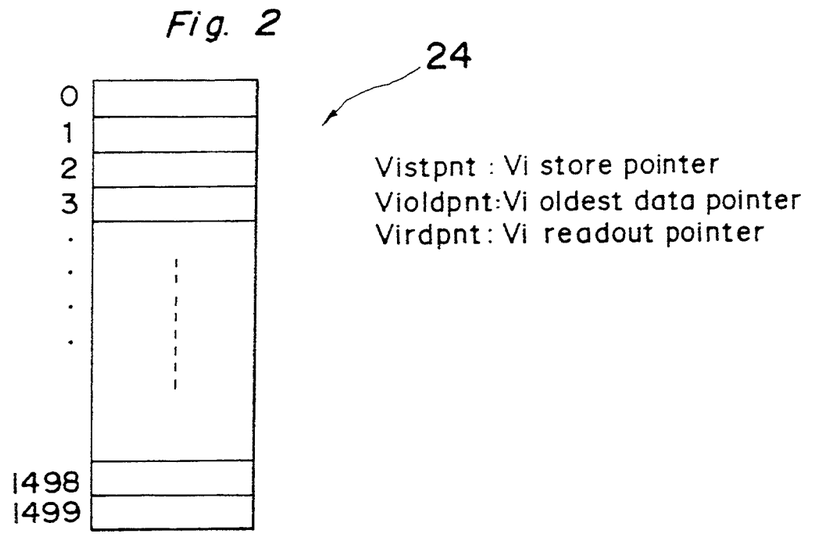
FIG. 2 shows a ring buffer incorporated in the infusion apparatus shown in FIG. 1.

FIG. 2 illustrates the ring buffer 24. Assuming that the first address of the ring buffer 24 is 0 and the last address is 1499 and that the ring buffer 24 is now in an initial state in which no data is stored, accumulated infusion fluid volumes are sequentially written to the ring buffer 24 in order of time from the first address O to the last address 1499. Therefore, the oldest data Vi which was obtained from 25 hours ago until 24 hours and 59 minutes ago is stored at address 0. Once the ring buffer 24 stores accumulated infusion fluid volumes Vi at all of 1500 addresses, a currently obtained accumulated infusion fluid volume Vi is stored at address 0 and a next accumulated infusion fluid volume Vi is then stored at address 1 and so on. Thus, the ring buffer 24 can always keep the Vi values written thereinto in the last 25 hours.

The following describes pointers used to designate addresses of the ring buffer 24 for write and readout operations. As described above, the ring buffer 24 has a size $N = 1500$. The ring buffer 24 has three pointers: 1) a pointer Vistpnt for indicating either an address at which an accumulated infusion fluid volume Vi is to be stored or an address at which the newest accumulated infusion fluid volume V1 is stored, 2) a pointer Violdpnt for pointing to an address where the oldest Vi value is stored, and 3) a pointer Virdpnt for pointing to an address at which the ring buffer 24 stores an accumulated infusion fluid volume Vi to be read out. Initial values of the pointers are Vistpnt = 1499, and Violdpnt = Virdpnt = 0. The address pointers Vistpnt, Violdpnt, and Virdpnt are appendant to the ring buffer 24 and backed up by the lithium battery 27. The initial values of the pointers are set at the time of starting the operation of the clock 26 immediately after the infusion apparatus is completed in a factory. Initialization of the pointers may be effected when the clock is restarted by a special function of the infusion apparatus or when there is need for the initialization for some reason. However, in a normal operation, the pointer values are only renewed by the CPU 18 and not initialized.

As described in connection with the conventional infusion apparatus, a current accumulated infusion fluid volume Vi is stored in the second storage section 22. The value Vi is incremented by one when a unit flow, i.e., an incremental unit of fluid (e.g., 1 ml) is detected by the rotation detector 10 (see FIG. 1). The current accumulated infusion fluid volume Vi stored in the second storage section 22 is written into the ring buffer 24 at an address pointed to by the pointer Vistpnt each time a unit time of one minute elapses. After the ring buffer 24 is loaded with Vi values at all the 1500 addresses thereof, the value of Violdpnt is set to be Violdpnt = Vistpnt + 1. However, when Violdpnt > 1499, the value of Violdpnt is reset to be Violdpnt = Violdpnt − 1500. The value of Virdpnt is set to be Virdpnt = Virdpnt − n + 1 when data Vi stored n minutes ago is accessed. However, the value of Virdpnt is reset to be Virdpnt = Virdpnt + 1500 if Virdpnt < 0.

The actual accumulated fluid value Vi read out from the second storage section 22 by the CPU 18 each time the clock 26 counts one minute is written into the ring buffer 24 at an address pointed by the pointer Vistpnt after the pointer Vistpnt is incremented by one. The pointer Vistpnt, whose initial value is 1499, is made to be 0 instead of 1500 when incremented by one. The value of the pointer Vistpnt starts from 0 in storing Vi values and is renewed to 1, 2, 3, ... up to 1499 each time the unit time of 1 minute elapses. During the above operation, because the oldest Vi value remains in address 0, the pointer Violdpnt keeps its initial value of 0. The pointer Vistpnt is set back to 0 one minute after storage of a Vi value in the ring buffer 24 at address 1499 to store a newest Vi value in address 0. Since the Vi value having been stored at address 0, which was the oldest one until then, is now lost, the pointer Violdpnt is renewed to 1 for the first time. Subsequently the pointer Violdpnt will be incremented by one at the time of incrementing the pointer Vistpnt by one. In other words, a relation of Violdpnt = Vistpnt + 1 holds (note that the value 1499 is incremented by one to be 0). By means of the pointers Vistpnt and Violdpnt, storage addresses of the newest and oldest Vi values in the ring buffer 24 can be known.

When reading out a Vi value, stored n minutes ago for instance, from the ring buffer 24 in response to a key-inputted request, Virdpnt is set to be Virdpnt = (Vistpnt − n) + 1. The reason for adding 1 to a value of (Vistpnt − n) is that an accumulated infusion fluid volume Vi obtained in the last one minute is stored at an address pointed to by the pointer Vistpnt (simply referred to as "address vistpnt" below). When a value n (n > 1500) is input, the value n is treated as n = 1500. When the ring buffer 24 is not fully loaded with Vi values, the pointer Violdpnt points to address O as described above. That is, the oldest data is stored at address 0. Therefore, in the case of Virdpnt < Violdpnt, Virdpnt is reset to be Virdpnt = Violdpnt. When the ring buffer 24 is fully loaded with Vi values, Virdpnt is reset at 1499 (Virdpnt = 1499) if Virdpnt = (Vistpnt − n) + 1 = −1.

The CPU 18 reads out the Vi value pointed to by the pointer Virdpnt from the ring buffer 24 to display the value on the display unit 3.

Figure 3:
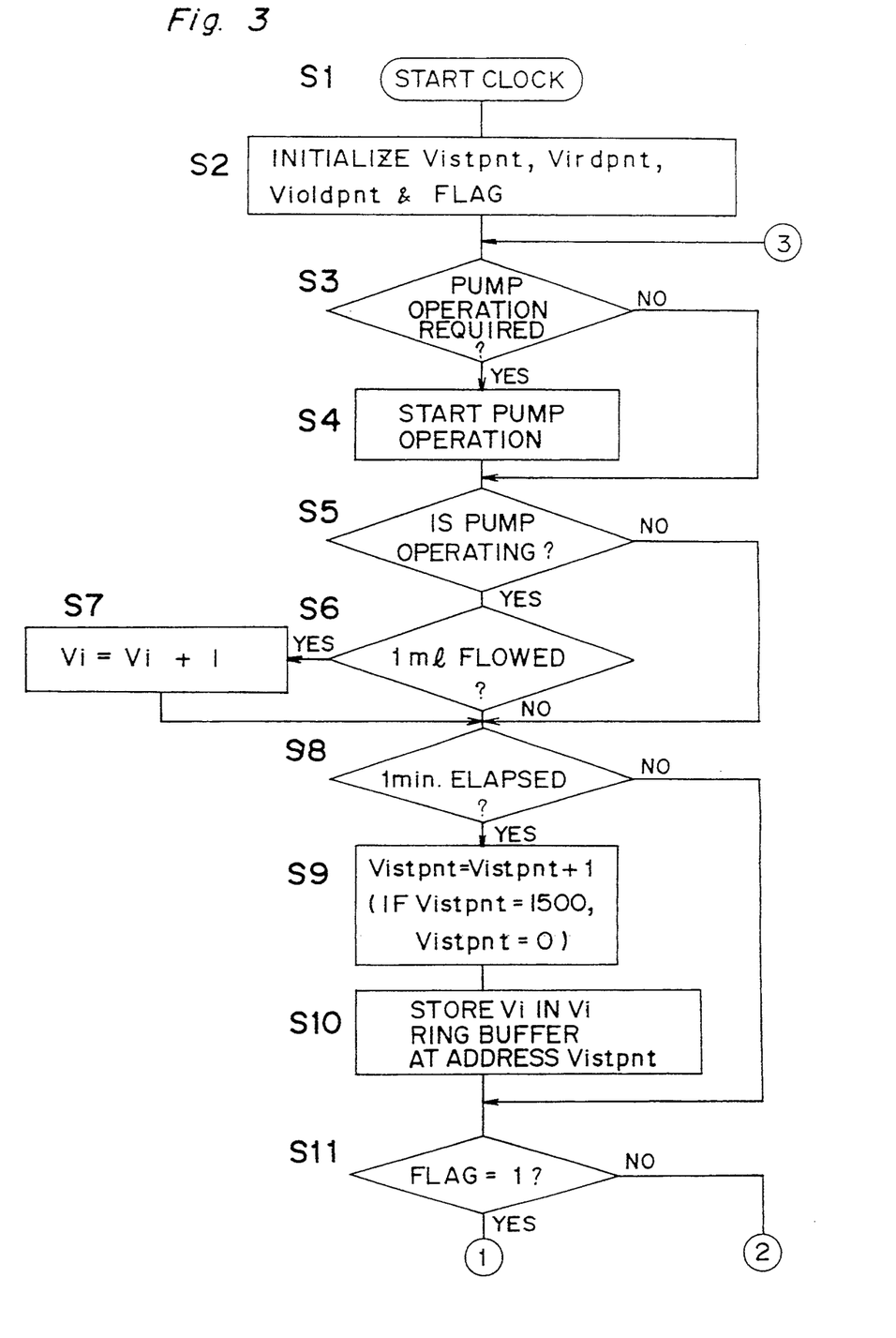
FIG. 3 is flowchart showing the operation of the infusion apparatus shown in FIG. 1.
Figure 4:
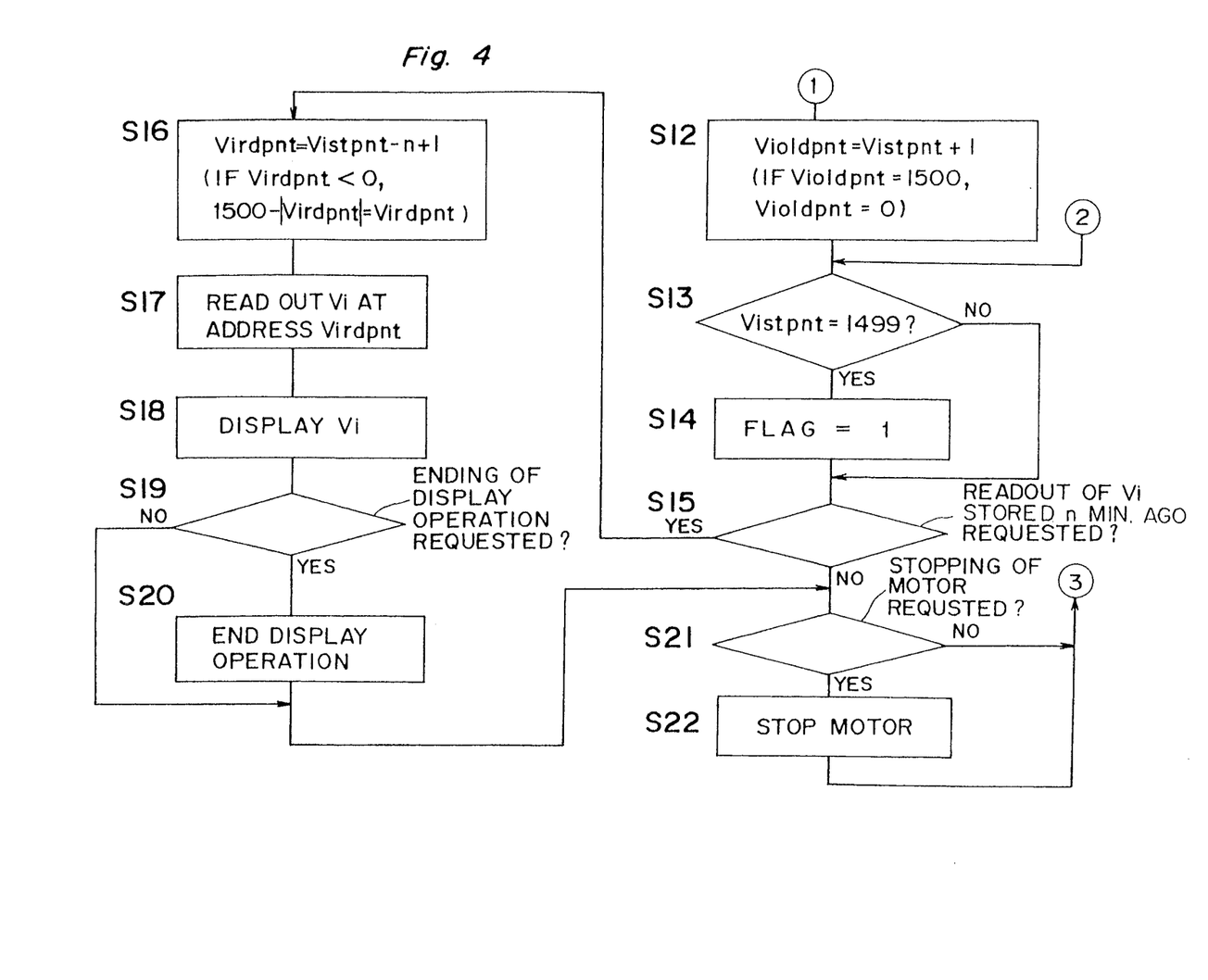
FIG. 4 is a flowchart continued from the flowchart shown in FIG. 3.

The following describes the operation of the present embodiment with reference to the flowcharts shown in FIGS. 3 and 4.

First, the clock 26 starts to operate at step S1. The above step is executed in the shipping stage of the infusion apparatus from the factory or at the time of resetting the clock 26 in a special mode, however, the step is normally not executed whether the infusion apparatus is turned on or off. Then the pointers Vistpnt, Virdpnt, and Violdpnt are initialized at step S2 as described hereinbefore. A flag indicates that the ring buffer 24 is fully loaded with Vi values at the 1500 addresses, when the flag is set at 1. An initial value of the flag is 0. It is then checked at step S3 whether or not there is a key input requesting to start the operation of the pump mechanism 8, i.e., to start the fluid delivery or infusion. If yes, the pump is started at step S4. When the pump is in operation at step S5, the program proceeds to step S6 at which it is checked whether or not an incremental unit of fluid (1 ml in this case) has been delivered. If yes, the program proceeds to step S7 at which the value Vi is incremented by one. Then it is checked at step S8 whether or not a unit time of the clock, i.e., one minute has elapsed. When it is determined that one minute has elapsed, the pointer Vistpnt for storing the Vi value into the ring buffer is incremented by one (Vistpnt=Vistpnt+1) at step S9. When the result of increments reaches 1500, resetting of Vistpnt at 0 (Vistpnt=0) is effected as described above. Thereafter, an actual accumulated infusion fluid volume Vi in the second storage section 22 is written into the ring buffer 24 at the address Vistpnt at step S10.

Then the flag value is checked at step S11. When flag=1, i.e., when 1500 Vi values are stored in the ring buffer 24, the pointer to the oldest Vi value must be renewed at step S12 as a result of the new value storage effected at step S10. Specifically, the pointer Violdpnt is incremented by one. When the result is 1500, Violdpnt is reset to be 0 (Violdpnt=0). Then it is checked at step S13 whether or not Vistpnt is 1499, i. e., whether or not the pointer Vistpnt is pointing to the maximum address of the ring buffer 24. When the pointer is pointing to the address 1499, the fact indicates that the 1500th Vi value got stored in the ring buffer 24 at step S10. Therefore, the flag is set at 1 (flag=1) at step S14. This may be not the first time that the Vistpnt=1499 state occurs. If it is the second or subsequent occurrence of such a state, however, the flag has already set at 1. In such a case, resetting of the flag at 1 has no problem.

Then it is checked at step S15 whether or not there was a key input requesting to read out a Vi value getting stored n minutes ago. If such a key input occurred, the program proceeds to step S16 at which a value of the pointer Virdpnt for reading out the Vi value is calculated in a manner as described above. It is to be noted that when the calculation gives Virdpnt<0, a further calculation of Virdpnt=1500−Virdpnt is executed. Then the Vi value stored at an address pointed to by the pointer Virdpnt (simply referred to as "address Virdpnt" below) is read out from the ring buffer at step S17 and the readout Vi is displayed on the display unit 3 at step S18. It is checked at step S19 whether the display operation should be ended or not. If yes, the display operation is ended at step S20. When a request for stopping the motor is detected at step S21, the motor is stopped at step S22.

As apparent from the above description, the storage of each Vi value into the ring buffer 24 is performed only according to the clock 26, irrespective of whether the infusion apparatus is in an ON state or OFF state or whether or not the fluid delivery is currently effected. Therefore the infusion apparatus always keeps the newest 1500 Vi values stored in the last 25 hours.

Figure 5:
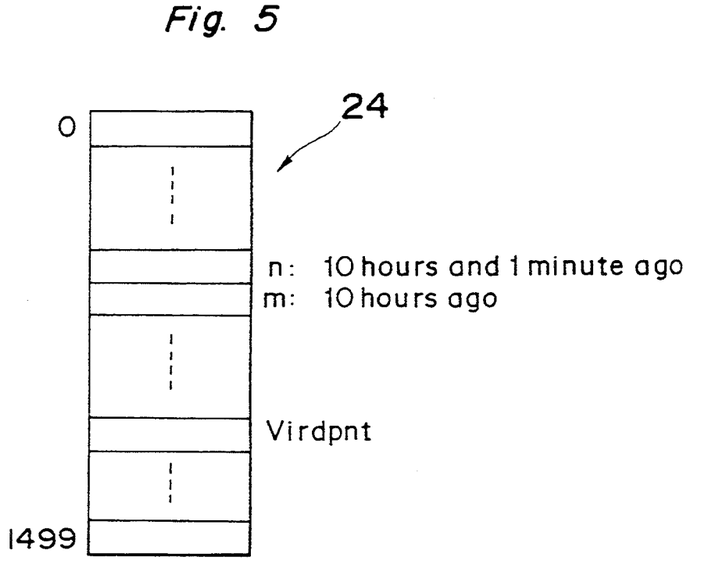
FIG. 5 is an illustration for explaining the operation of reading contents stored in the ring buffer of FIG. 2.

Referring now to FIG. 5, the renewed accumulated infusion fluid volume Vi stored in the second storage section 22 is written into the ring buffer as it is, upon elapse of every unit time. When a doctor or nurse reads out two Vi values, for example, an older value Vi(n) stored 10 hours and 1 minute ago and a less old value Vi(m) stored 10 hours ago, from the ring buffer 24, a fluid volume dv delivered for one minute between those two times can be obtained from an equation dv=Vi(m)−Vi(n). It is to be noted that m and n described above indicate respective pointers for calling the Vi value stored 10 hours ago and the Vi value stored 10 hours and 1 minute ago, and the pointer values can be derived from the equations of m=Vistpnt−60*10+1 and n=Vistpnt−(60*10+1)+1 as described hereinbefore.

Generally, when two values of dv(l) and dv(k) indicating the delivery per minute in different times of the past are compared with each other and the coincidence results, it can be considered that the fluid delivery, that is, the infusion was carried out at the same infusion rate at those different times. When the two values are different, it is found that fluid was delivered at different rates and that a different amount of medication was administered to the patient. The doctor or nurse can read out a necessary number of necessary data of the past to determine the detail for the next infusion operation.

The reason why the delivery dv per minute is not stored in the Vi ring buffer 24 is as follows. If such an algorithm is adopted, it will be necessary to hold the preceding accumulated infusion fluid volume Viold stored 1 minute ago in addition to the actual accumulated infusion fluid volume Vi, carry out a calculation dv=Vi−Viold after the elapse of every unit time, store the value dv in the ring buffer, and replace Viold with Vi for the calculation of the next 1 minute delivery. In addition, in order to obtain an accumulated infusion fluid volume at the time of 10 hours ago, it will be necessary to add up dv values read out from the ring buffer from the address Violdpnt to the address Virdpnt. This method will take much time in adding the values read out from the ring buffer and require a lot of operations in comparison with the case of the present embodiment where accumulated infusion fluid volumes Vi are stored into the ring buffer as they are, thus producing less advantages. However, even in such a case, the same effect will result.

As can be seen from the above, the present invention can release the operator of the infusion apparatus from additional simultaneous work such as manual recording of the adopted infusion rates and delivered fluid volumes and eliminate possibility of recording errors, thus producing a good therapeutic effect. The operator such as a doctor or a nurse can readily get correct infusion data of the past from the memory. Therefore, it is possible for the doctor or nurse to immediately determine the detail of the subsequent infusion based on the read-out previous infusion data and taking the condition of the patient into account.

The invention being thus described, it will be clear to one skilled in the art that the same may be varied in many ways. Such variations are not to be regarded as a departure from the spirit and scope of the invention, and all such modifications as would be obvious to one skilled in the art are intended to be included within the scope of the following claims.

What is claimed is:

1. An infusion apparatus for infusing an infusion fluid into a patient through an administration tube, comprising:

a peristaltic pump mechanism for peristaltically pumping the infusion fluid in the administration tube to deliver the infusion fluid toward the patient;

clock means for counting a predetermined unit time;

accumulating means for accumulating data representing a unit flow of said infusion fluid delivered by said pump mechanism to measure an accumulated infusion fluid volume each time said clock means counts said predetermined unit time;

storage means for storing a plurality of accumulated infusion fluid volumes measured by said accumulating means, each accumulated infusion fluid volume being written in sequence into said storage means each time said clock means counts said predetermined unit time;

accessing means for reading out any one of said accumulated infusion fluid volumes stored in said storage means at a request of an operator;

display means for displaying the accumulated infusion fluid volume read out by said accessing means; and means for inputting said request.

2. The apparatus of claim 1, wherein said storage means comprises a ring buffer which always holds a predetermined number of newest accumulated infusion fluid volumes measured in a predetermined period of time preceding a current time.

3. The apparatus of claim 1, wherein said storage means stores said plurality of accumulated infusion fluid volumes in one-to-one correspondence with a plurality of different times at which said plurality of accumulated infusion fluid volumes were measured.

4. The apparatus of claim 1, wherein the accumulated infusion fluid volumes stored in the storage means are accessed and displayed in order of time or in arbitrary order.

5. The apparatus of claim 1, wherein said clock means is powered independent of said apparatus.

* * * * *